(12) United States Patent
Swartz et al.

(10) Patent No.: US 8,183,010 B2
(45) Date of Patent: May 22, 2012

(54) CELL-FREE SYNTHESIS OF MEMBRANE BOUND POLYPEPTIDES

(75) Inventors: James Robert Swartz, Menlo Park, CA (US); Jessica Wuu, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/089,596

(22) PCT Filed: Oct. 31, 2006

(86) PCT No.: PCT/US2006/042583
§ 371 (c)(1),
(2), (4) Date: Aug. 5, 2008

(87) PCT Pub. No.: WO2007/053655
PCT Pub. Date: May 10, 2007

(65) Prior Publication Data
US 2009/0029414 A1      Jan. 29, 2009

Related U.S. Application Data

(60) Provisional application No. 60/732,437, filed on Oct. 31, 2005.

(51) Int. Cl.
*C12P 21/00* (2006.01)
(52) U.S. Cl. ...................... 435/68.1; 435/390
(58) Field of Classification Search .......... None
See application file for complete search history.

(56) References Cited

U.S. PATENT DOCUMENTS

| 6,337,191 B1 | 1/2002 | Swartz et al. |
| 7,338,789 B2 * | 3/2008 | Swartz et al. ............. 435/71.2 |
| 2004/0209321 A1 | 10/2004 | Swartz et al. |
| 2005/0054032 A1 | 3/2005 | Voloshin et al. |
| 2005/0054044 A1 | 3/2005 | Swartz et al. |

FOREIGN PATENT DOCUMENTS

| WO | 2004/016778 | 2/2004 |
| WO | 2005/052117 | 6/2005 |
| WO | 2005/098048 | 10/2005 |

OTHER PUBLICATIONS

Calhoun; et al., "Energizing Cell-Free Protein Synthesis With Glucose Metabolism", Biotechnol. Bioeng. (2005), 90(5):606-13.
Jewett; et al., "Mimicking the *Escherichia coli* Cytoplasmic Environment Activities Long-Lived and Efficient Cell-Free Protein Synthesis", Biotechnol. Bioeng. (2004), 86(1):19-26.
Jewett; et al., "Prokaryotic Systems for In Vitro Expression", Gene Cloning and Expression Technologies (2002), pp. 391-411.
Kuruma; et al., "Development of a Minimal Cell-Free Translation System for the Synthesis of Presecretory and Integral Membrane Proteins", Biotechnol. Prog. (2005), 21(4):1243-1251.
Lin; et al., "Genetic Reconstruction of the Aerobic Central Metabolism in *Escherichia coli* for the Absolute Aerobic Production of Succinate", Biotechnol. Bioeng. (2005), 89(2):148-56.
Noireaux; et al., "A vesicle bioreactor as a step toward an artificial cell assembly", PNAS (2004), 101(51):17669-17674.
Tai; et al., "In vitro protein translocation into *Escherichia coli* inverted membrane vesicles", Methods in Cell Biology (1991), 34:167-187.

* cited by examiner

*Primary Examiner* — Kagnew H Gebreyesus
(74) *Attorney, Agent, or Firm* — Bozicevic, Field & Francis LLP; Pamela J. Sherwood

(57) ABSTRACT

Methods are provided for the utilization of bacterial cell-free extracts in the synthesis of high yields of membrane-associated polypeptides.

13 Claims, 6 Drawing Sheets

CELL-FREE SYNTHESIS OF MEMBRANE BOUND POLYPEPTIDES

FEDERALLY SPONSORED RESEARCH AND DEVELOPMENT

This invention was made with Government support under contract NAG8-1843 awarded by the NASA Marshall Space Flight Center. The Government has certain rights in this invention.

BACKGROUND OF THE INVENTION

Protein synthesis is a fundamental biological process that underlies the development of polypeptide therapeutics, diagnostics, and industrial enzymes. With the advent of recombinant DNA (rDNA) technology, it has become possible to harness the catalytic machinery of the cell to produce a desired protein. This can be achieved within the cellular environment or in vitro using extracts derived from cells.

Cell-free protein synthesis offers several advantages over in vivo protein expression methods. Cell-free systems can direct most, if not all, of the metabolic resources of the cell towards the exclusive production of one protein. Moreover, the lack of a cell wall in vitro is advantageous since it allows for control of the synthesis environment. For example, tRNA levels can be changed to reflect the codon usage of genes being expressed. The redox potential, pH, or ionic strength can also be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.

Among the proteins of interest for cell-free synthesis, many either span or are anchored to membranes. These proteins and other biomolecules incorporated into membranes surrounding cells and organelles moderate a wide variety of cellular functions. Furthermore, many lipids and glycolipids are targets for, or activate, protein functions.

For example, about half of potential pharmaceutical targets are membrane proteins, e.g. ion channels and G protein coupled receptors, which have been difficult to utilize in drug screening and design assays. Because of their location in membranes, these proteins are frequently difficult to purify and characterize. They are also difficult to obtain in large quantities, and recombinant DNA methods often fail to provide large amounts of properly folded membrane proteins, in part because overexpression of membrane proteins is generally toxic to living cells, thus limiting the yield.

To avoid this toxicity, in vitro techniques have been attempted to produce higher yields of protein. However, reports have shown either low yields, similar or less than those obtained in vivo; high yields, but where most of the protein is aggregated and must be refolded post-translationally; or high yields where the protein has been synthesized into detergents or liposomes without using the natural folding pathway, raising a question of whether these systems produce membrane proteins that are authentically folded.

One of the major limitations in studying membrane proteins has been the general difficulty in producing significant quantities of correctly folded protein. The present invention addresses this need.

Relevant Literature

U.S. Pat. No. 6,337,191 B1; Swartz et al. U.S. Patent Published Application 20040209321; Swartz et al. International Published Application WO 2004/016778; Swartz et al. U.S. Patent Published Application 2005-0054032-A1; Swartz et al. U.S. Patent Published Application 2005-0054044-A1; Swartz et al. International Published Application WO 2005/052117. Calhoun and Swartz (2005) Biotechnol Bioeng 90(5):606-13; Jewett and Swartz (2004) Biotechnol Bioeng 86(1):19-26; Jewett et al. (2002) Prokaryotic Systems for In Vitro Expression. In: Weiner M, Lu Q, editors. Gene cloning and expression technologies. Westborough, Mass.: Eaton Publishing. p 391-411; Lin et al. (2005) Biotechnol Bioeng 89(2): 148-56.

SUMMARY OF THE INVENTION

Methods are provided for high yield cell-free synthesis of membrane associated proteins. In the methods of the invention, vesicles are added to a cell-free synthesis reaction, providing for direct insertion of the nascent polypeptide into a biological membrane, thereby providing for folding in a membrane environment. Generally the synthesis is performed as a coupled transcription and translation reaction to allow for co-translational folding. These methods provide for high yields of active protein. The method may further include the isolation of the synthesized protein in a membrane bound state.

In some embodiments, the methods of the invention further include providing signal recognition particles (SRP) to the reaction. The particles may be exogenously produced, or co-synthesized in the reaction mix. A docking protein for the SRP may also be included.

In a preferred embodiment, the synthesis reaction conditions provide for in vitro activation of oxidative phosphorylation. The activation of oxidative phosphorylation may be evidenced by the ability of the reaction mixture to regenerate ATP in the absence of conventional secondary energy sources. The activation of oxidative phosphorylation can also be demonstrated by the sensitivity of the reaction mixture to specific inhibitors of this pathway. Such reactions are substantially free of polyethylene glycol.

Production of high yields of active membrane associated proteins is useful in a variety of methods, including screening for drug candidates that interact with pharmacologically relevant membrane protein targets such as multi-drug transporters or signaling proteins; development of membrane protein-based biosensors; strategies for detoxification wherein the vesicles import toxins for subsequent vesicle recovery and removal; and the like.

DETAILED DESCRIPTION OF THE EMBODIMENTS

Figure 1:
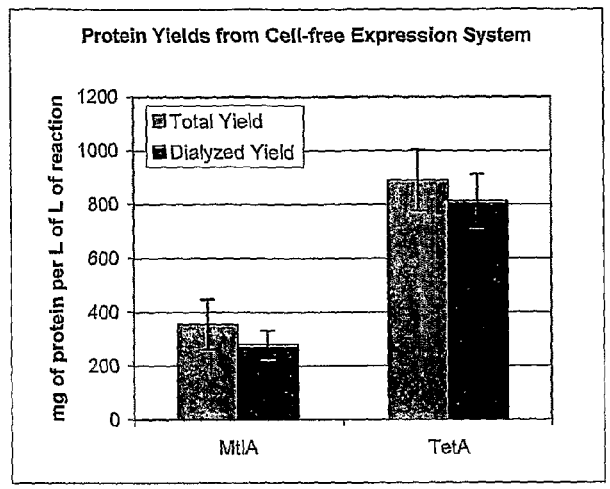
FIG. 1 Total and dialyzed protein yields from cell-free reactions synthesizing MtlA or TetA.

High yield synthesis of membrane-associated proteins is accomplished by performing coupled transcription and translation reactions in a cell-free reaction, where membrane vesicles are present, and where the reaction conditions provide for in vitro activation of oxidative phosphorylation. The protein of interest is synthesized in a manner that allows co-translational folding and direct insertion of the nascent polypeptide into a membrane, thereby providing for folding in a membrane environment. The method may further include the isolation of the synthesized protein in a membrane bound state.

The methods of the invention provide for high yields of active protein, which may be greater than the yield that can be achieved with in vivo expression systems. In one embodiment of the invention, the yield of active membrane associated protein is greater than the yield of the protein of interest in vivo. In other aspects, the yield of active membrane-associated protein is at least about 50 μg/ml of reaction mixture; at least about 100 μg/ml of reaction mixture; at least about 250 μg/ml of reaction mixture; or more.

The methods of the present invention provide for membrane associated proteins that have biological activity comparable to the native protein. One may determine the specific activity of a protein in a composition by determining the level of activity in a functional assay, quantitating the amount of protein present in a non-functional assay, e.g. immunostaining, ELISA, quantitation on coomasie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

One aspect of the high yield is that the proteins are directly inserted into membranes during synthesis. Therefore the isolation of active membrane associated protein does not require the use of artificial liposomes, or refolding of the protein. The protein may be directly isolated from the reaction mixture in any method that preserves the membrane association. Methods of protein purification that maintain membrane integrity are known in the art. Typically, mild detergents such as laurel glucosides or maltosides are used to distribute the properly folded membrane spanning proteins into micelles containing one or only a few protein molecules. These micelles are then separated based on their protein cargoes to provide purified membrane spanning proteins (see Loll, P J, J. of Structural Biology, 142:144-153; 2003), herein specifically incorporated by reference.

In some embodiments, the methods of the invention further include providing signal recognition particles (SRP) to the reaction. The particles may be exogenously produced, or co-synthesized in the reaction mix. Docking protein (SR) may also be included.

Activation of oxidative phosphorylation is obtained by a combination of reaction conditions, which conditions may include, without limitation, the use of biological extracts derived from bacteria grown on a glucose containing medium; an absence of polyethylene glycol; and optimized magnesium concentration. The system does not require the addition of commonly used secondary energy sources, which energy sources typically contain high energy phosphate bonds, such as phosphoenolpyruvate, creatine phosphate, acetyl phosphate, glucose-6-phosphate, pyruvate or glycolytic intermediates. The reaction may be further improved by employing ions and compounds in the cell-free reaction mixture that are commonly found in the *E. coli* cytoplasm.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "desired protein" or "selected protein" are used interchangeably and refer generally to any peptide or protein having more than about 5 amino acids, which is membrane associated by virtue of a membrane inserted polypeptide. The polypeptides may be homologous to, or preferably, may be exogenous, meaning that they are heterologous, i.e., foreign, to the bacteria from which the bacterial cell-free extract is derived, such as a human protein or a yeast protein produced in the bacterial cell-free extract.

Membrane associated proteins. Membrane proteins can be classified into two broad categories, integral (intrinsic) and peripheral (extrinsic), based on the nature of the membrane-protein interactions. For the purposes of the present invention, membrane associated proteins are typically integral membrane proteins, also called intrinsic proteins, which have one or more segments that are embedded in the phospholipid bilayer. Most integral proteins contain residues with hydrophobic side chains that interact with fatty acyl groups of the membrane phospholipids, thus anchoring the protein to the membrane. Most integral proteins span the entire phospholipid bilayer. These transmembrane proteins contain one or more membrane-spanning domains as well as domains, from four to several hundred residues long, extending into the aqueous medium on each side of the bilayer.

Some proteins are bound only to the membrane surface, whereas others have one region buried within the membrane and domains on one or both sides of it. Protein domains on the extracellular membrane surface are generally involved in cell-cell signaling or interactions. Domains within the membrane, particularly those that form channels and pores, move molecules across the membrane. Domains lying along the cytosolic face of the membrane have a wide range of functions, from anchoring cytoskeletal proteins to the membrane to triggering intracellular signaling pathways.

G protein-coupled receptors are integral membrane proteins that possess seven membrane-spanning domains or transmembrane helices. The extracellular parts of the receptor can be glycosylated. These extracellular loops also contain two highly conserved cysteine residues which build disulfide bonds to stabilize the receptor structure. Some seven transmemebrane helix proteins that resemble G proteins may contain different functional groups, such as entire ion channels, within their protein. While in other types of receptors that have been studied ligands bind externally to the membrane, the ligands of G-protein-coupled receptors typically bind within the transmembrane domain.

Another important class of membrane-associated proteins are ion channels. All ion channels are complexes of transmembrane proteins, sometimes they contain cytoplasmic subunits, often they are glycosylated. Ion channels can be classified according to which chemical or physical modulator controls their gating activity. Thus we have different groups of channels, including: ligand gated channels/neurotransmitters; voltage gated channels/transmembrane potential (electric field); second messenger gated channels/nucleotides, G-proteins; mechanosensitive channels/osmotic pressure or membrane curvature; gap junctions, porins/not gated. Channels are also ion selective. They can discriminate between size and charge of the permeant molecule.

In vitro synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

The Cytomin™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium.

Another important change in the reaction mixture is the substantial absence of polyethylene glycol (PEG). A conventional reaction mixture (for example, see Kim and Swartz, 2001) contains about 2% polyethylene glycol 8000. However it is found that this diminishes the yield. Typically PEG will be present in not more than trace amounts, for example less than 0.1%, and may be less than 0.01%. In the present methods, the molecules spermidine and putrescine are used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 20 mM, usually not more than about 15 mM. Other changes that may enhance synthesis include the omission of HEPES buffer and phosphoenol pyruvate from the reaction mixture.

The system can be run under aerobic and anaerobic conditions. Oxygen may be supplied, particularly for reactions larger than 15 μl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), NAD+, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Vesicles are added to the reaction mix. Vesicles may purified from the organism from which the extract is derived (see Muller and Blobel (1984) "In vitro translocation of bacterial proteins across the plasma membrane of *Escherichia coli*", PNAS 81:7421-7425); or isolated from any other suitable cell, e.g. mammalian cells including cells from the species of target protein; or synthetic. Vesicles are typically added at a concentration of 0.1 to 5 mg/ml lipids, more preferably about 0.4 to 2.5 mg/ml. Vesicles may be purified by sucrose density gradient centrifugation or by other means known in the art. Vesicle preparation methods include, without limitation: homogenization, French press, extrusion, freeze/thaw, sonication, osmotic lysis, lysozyme/EDTA treatment, and the like. Other components that affect membrane protein insertion or folding may be added to the cell-free reaction mixture, including SRP, Ffh, 4.5S RNA, FtsY, and SecA.

Signal recognition particle. Co-translational targeting of secretory and membrane proteins to the prokaryotic plasma membrane or eukaryotic endoplasmic reticulum is mediated by a ribonucleoprotein complex, the signal recognition particle (SRP), and its membrane-associated receptor (SR). SRP binds to signal sequences of nascent proteins as they emerge from the exit tunnel of the ribosome. The resulting targeting complex, composed of the SRP and the ribosome-nascent chain complex (RNC), then docks with the SR in a GTP-dependent manner. Passing through a complex series of conformational states, SRP and SR deliver the RNC to the translocon, which in turn mediates protein translocation across or integration into the membrane. As translocation proceeds, the signal sequence may be cleaved by signal protease and the polypeptide released into the ER lumen. Alternatively, the protein can insert into the membrane to form a membrane spanning protein.

The bacterial SRP has a simple composition as compared to its eukaryotic counterpart. It contains only a single protein homologous to SRP54 (termed Ffh) and a single RNA molecule, between 80 and 200 nts in size, e.g. a 110-nucleotide 4.5S RNA in *E. coli*. In bacteria and archaea, SRs are single-subunit proteins, also named FtsY. Bacterial SRs are peripherally associated with membranes.

The SRP and docking protein (SR) are optionally included in the reaction mix for the methods of the invention. These may be provided through co-expression of the components in the reaction mix, or through exogenous addition. Where the components are provided by co-expression, a vector encoding the Ffh protein and the 4.5S RNA are provided. The FtsY protein may also be co-expressed. Co-expression may be sequential or simultaneous. Alternatively, these components may be produced and isolated from in vitro or in vivo expression, and added to the mixture; or may be over-produced in the bacteria from which the extracts are derived.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein are important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The synthesis of membrane-associated protein may be followed by direct isolation of the active, membrane associated forms, i.e. in the absence of refolding or post-translational introduction of membranes. The separation procedure will utilize conditions that maintain membrane integrity, as is known in the art.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be coupled to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art.

Methods For Synthesis

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 1 μl and not more than about 15 μl, or in a scaled up reaction, where the reaction volume is at least about 15 μl, usually at least about 50 μl, more usually at least about 100 μl, and may be 500 μl, 1000 μl, or greater. In most cases, individual reactions will not be more than about 10 ml, although multiple reactions can be run in parallel. However, in principle, reactions may be conducted at any scale as long as sufficient oxygen (or other electron acceptor) is supplied when needed.

In addition to the above components such as cell-free extract, genetic template, and amino acids, materials specifically required for protein synthesis may be added to the reaction. These materials include salt, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or sulfuric acid). One or more of such salts may have amino acids as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation. Vesicles containing the product may also be continuously isolated, for example by affinity adsorption from the reaction mixture either in situ or in a circulation loop as the reaction fluid is pumped past the adsorption matrix.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Kits for the practice of the subject methods may also be provided. Such kits may include bacterial extracts for protein synthesis, buffers appropriate for reactions where oxidative phosphorylation is activated, and vesicles. Kits may also include vectors for protein synthesis, including vectors for expression of SRP and SR proteins; where the vectors may comprise promoter systems useful in bacterial extracts.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

The protein synthesis reaction for these examples uses the CytoMim™ protocol described in WO 2004/016778, herein specifically incorporated by reference, with slight modifications. The components of this reaction include 13.3 µg/mL template plasmid, 1.2 mM AMP, 0.86 mM CMP, 0.86 mM GMP, 0.86 mM UMP, 34 µg/mL folinic acid, 170.6 µg/mL *E. coli* tRNA mixture, 2 mM each of 20 unlabeled amino acids, 0.33 mM nicotinamide adenine dinucleotide, 0.27 mM coenzyme A, 1 mM putrescine, 1.5 mM spermidine, 4 mM sodium oxalate, 1 mM dithiothreitol, 10 mM ammonium glutamate, 130 mM potassium glutamate, 8 mM magnesium glutamate, 10 mM potassium phosphate pH 7.2, 12 µM [$^{14}$C]-leucine, 0.1 mg/mL T7 RNA polymerase, 0.24 volumes of *E. coli* S30 extract, and 0.41 volumes of vesicle solution (detailed below). T7 RNA polymerase is prepared as described by Grodberg and Dunn (J of Bacteriology, 170:1245-1253; 1988). *E. coli* S30 extract is prepared from the strain KC6 (A19 ΔtonA ΔtnaA ΔspeA ΔendA ΔsdaA ΔsdaB ΔgshA met*) (Calhoun and Swartz, Biotechnology Progress 2005. 21 (4): p. 1146-53) grown according to Zawada, et al. in *Fermentation Biotechnology*, B. Saha, Editor. 2003, American Chemical Society: Washington, D.C. p. 142-156, and prepared according to Jewett, et al. in *Gene Cloning and*

*Expression Technologies*, M. Weiner and Q. Lu, Editors. 2002, Eaton Publishing: Westborough, Mass. p. 391-411.

The vesicle solution is prepared using a method adapted from Muller and Blobel (1984) Proc Natl Acad Sci U S A, 81 (23): p. 7421-5, and Osborn, et al (1972) J Biol Chem, 1972. 247 (12): p. 3962-72. KC6 cells are resuspended and washed in 20 mM Tris-HCl pH 8.0, 1 mM EDTA. The final cell pellet is resuspended in 1 mL of the same buffer per gram of cells and incubated on ice with 0.2 mg/mL of lysozyme for 15 min. After incubation, the cell solution is passed through an Avestin homogenizer three times at 20000 psi. Unbroken cells and debris are removed by two centrifugations at 30000×g for 20 min each. Then the vesicles are collected by ultracentrifugation (154000×g, 1.5 hr), and pelleted again through 0.5 mL/$g_{cells}$ of a solution containing 250 mM sucrose in buffer H (20 mM HEPES-KOH pH 7.5, 1 mM DTT, 5 mM EDTA) at 231000×g for 1 hr. These crudely purified vesicles are resuspended in 20% (w/w) sucrose in buffer H and loaded on top of a step gradient containing layers of 50%, 45%, 40%, 35%, 30%, and 25% (w/w) sucrose in buffer H. After ultracentrifugation for 24 hrs at 114000×g, the fractions containing inner membrane vesicles (as detailed in Spencer et al. (1974) J Bacteriol, 117 (3): p. 947-53, or Langley et al. (1982) J Bacteriol, 152 (3): p. 1033-41) are collected. These vesicles are pelleted by ultracentrifugation at 231,000×g for 1 hr and finally resuspended to high concentration (1-2 mg/mL) in 20 mM HEPES-KOH pH 7.2, 60 mM KCl, 1 mM DTT.

The membrane proteins mannitol permease (MtlA) and the tetracycline pump (TetA) were synthesized by the methods of the invention. The plasmids pK7MtlA and pK7TetA, respectively, were used as templates encoding the genes under the control of T7 promoters.

After 6 hrs of synthesis at 37° C., the synthesized protein was quantified by measuring TCA-precipitable radioactivity using a liquid scintillation counter. FIG. 1 shows the total amount of MtlA and TetA produced during the cell-free reaction. Before further analysis, the reaction was crudely purified by dialysis with a 100 kDa MWCO dialysis bag against 500-1000 volumes of 10 mM Tris-HCl pH 8.0, 100 mM KCl, exchanged three times for at least 3 hours each time. The results in FIG. 1 show that virtually all the synthesized protein is retained during dialysis.

To determine if the synthesized protein was folded properly in the vesicle membranes, we exposed the dialyzed reaction mixture to 0.2 μg/μL of the non-specific protease, Proteinase K. Portions of the membrane protein that are not embedded in the membrane—such as cytoplasmic domains or large loops between transmembrane segments—are degraded more quickly by the protease as compared with segments within the membrane or in the vesicle interior. Thus, by observing the protein fragments generated by Proteinase K digestion over time, we can verify whether the protein has the expected topology that corresponds with proper folding.

Figure 2:
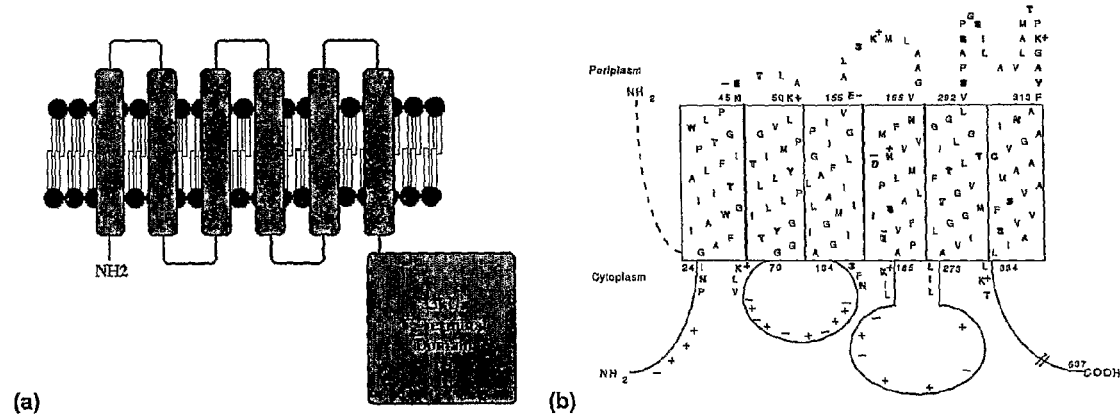
FIG. 2 (a) Topology of MtlA showing six transmembrane segments and a large C-terminal domain on the cytoplasmic side of the membrane. (b) Predicted topology of the transmembrane portion of MtlA. The largest cytoplasmic loop (K185-V273) encompasses 89 amino acids.
Figure 3:
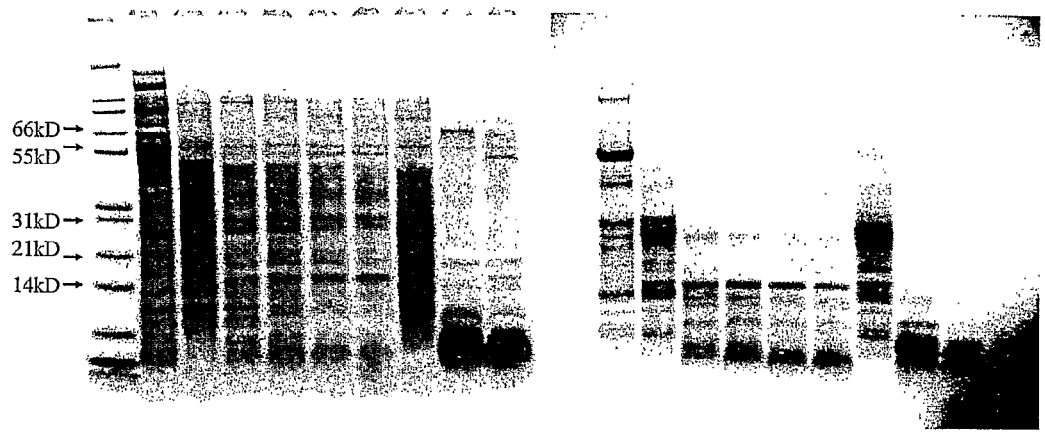
FIG. 3 Coomassie stained protein gel (left) and corresponding autoradiogram (right) of MtlA samples digested at 37° C. with Proteinase K. Abbreviations: Proteinase K (Prot K), lithium dodecyl sulfate (LDS).

MtlA is well suited for protease digestion analysis because it contains a large cytoplasmic domain (FIG. 2a) as well as a large cytoplasmic loop (FIG. 2b). FIG. 3 shows digested MtlA after incubation with Proteinase K at 37° C. for 0 to 60 min. During the early time points, a distinct band of approximately 30 kDa is formed. This corresponds well with a fragment containing only the six transmembrane segments, after degradation of the large cytoplasmic domain. As the digestion reaction proceeds, the 30 kDa band diminishes in favor of a 17 kDa band. This 17 kDa band is comparable to the expected fragment containing four transmembrane segments, obtained after digestion of the large 89-amino acid cytoplasmic loop. If the reaction is performed in the presence of lithium dodecyl sulfate (LDS) detergent which dissolves membranes, the MtlA bands are no longer protected from digestion; indicating that the protected bands are dependent on the presence of intact vesicle membranes. Thus, the observed band pattern demonstrates that a significant portion of the MtlA is properly folded in the vesicle membranes.

Figure 4:
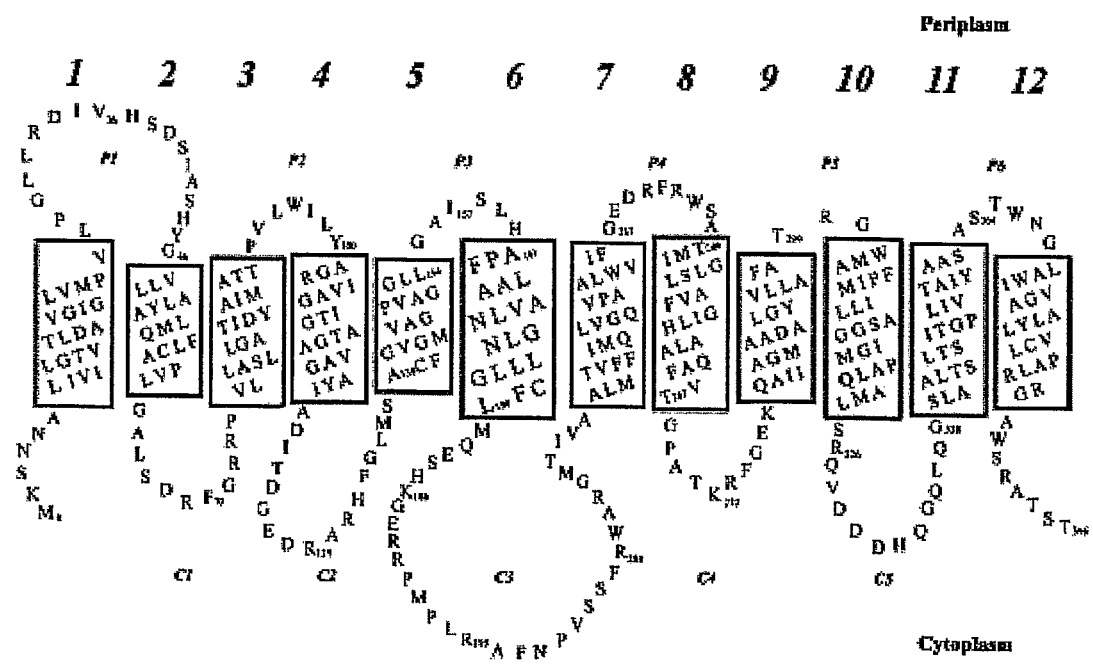
FIG. 4 Topology of TetA showing twelve transmembrane segments. The largest cytoplasmic loop (M181-A213) is only 33 amino acids.
Figure 5:
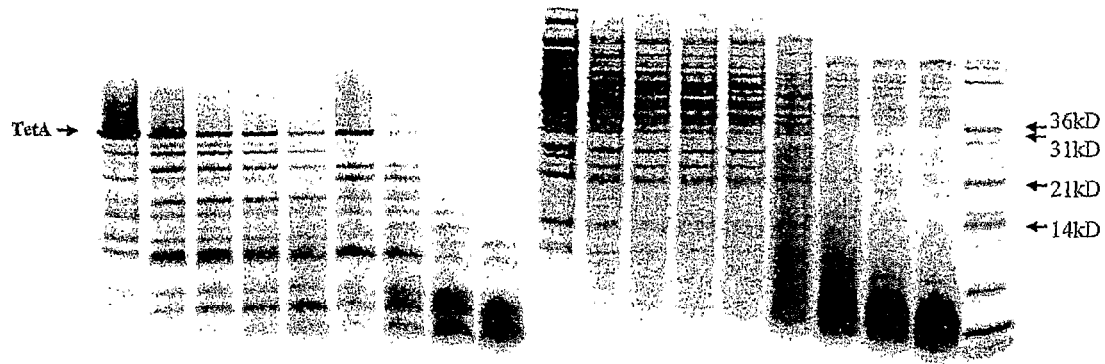
FIG. 5 Coomassie stained protein gel (right) and corresponding autoradiogram (left) of TetA samples digested at 25° C. with Proteinase K. Abbreviations: Proteinase K (Prot K), lithium dodecyl sulfate (LDS).

A similar analysis was performed with TetA. The topology of TetA, shown in FIG. 4, does not contain any large cytoplasmic domains or loops. Therefore, we focused on protection of the full-length TetA. FIG. 5 shows the band profile obtained after incubation with Proteinase K at 25° C. Even after 60 min, a significant fraction of full-length TetA is still present in the vesicles. However, if the membranes are dissolved with LDS detergent, the TetA is no longer protected from digestion. Thus, it appears that the TetA is embedded into the vesicle membranes.

Figure 6:
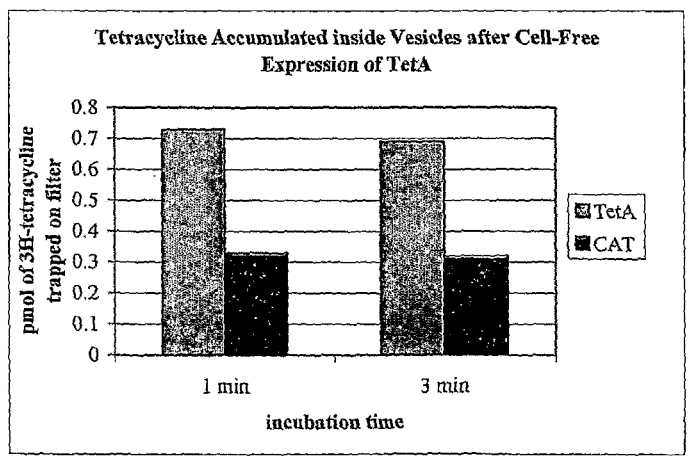
FIG. 6 Tetracycline accumulation inside vesicles present during TetA or CAT protein expression.

To further demonstrate that the TetA is properly folded, activity of the TetA protein was assayed. TetA is a proton-antiporter, using a proton gradient to drive transport of a metal-tetracycline complex across the membrane. To assay for TetA activity, first the TetA-containing vesicles were exposed to 13.3 mM NADH for 1 min at 37° C. in order to generate a proton gradient across the vesicle membrane. 10 μM [$^3$H]-tetracycline and 0.5 mM cobalt chloride were then added, and the reaction was further incubated for the times indicated in FIG. 6. The reactions are finally filtered and washed through a 30K molecular weight centrifugal filter to separate vesicle-associated tetracycline from free tetracycline in solution. FIG. 6 shows that more tetracycline accumulates within vesicles containing TetA, as compared to control vesicles obtained from a cell-free reaction producing the unrelated soluble protein chloramphenicol acetyl transferase (CAT). The control vesicles show tetracycline accumulation of approximately 3-13 μM within the vesicles, which is consistent with equilibrium driven diffusion of tetracycline across the lipid membrane. The vesicles containing TetA, however, are able to accumulate tetracycline even against a tetracycline concentration gradient, indicating that a significant portion of TetA is properly folded and active in the vesicles.

Figure 7:
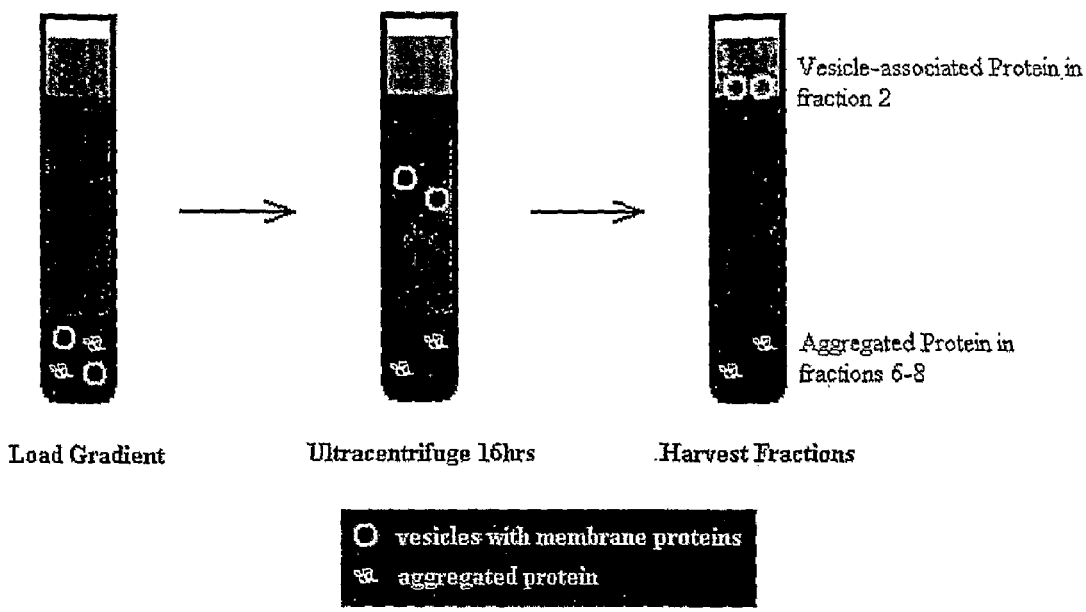
FIG. 7 Schematic of the sucrose flotation assay.
Figure 8:
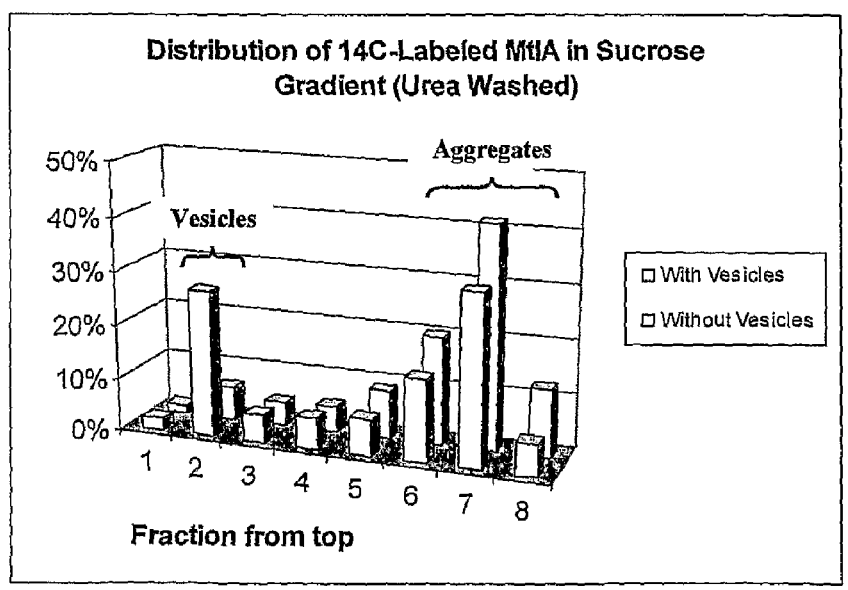
FIG. 8 Distribution of radiolabeled MtlA in sucrose floatation assays. Vesicle-associated MtlA floats up to fraction 2, while aggregated MtlA remains at the bottom of the gradient in fractions 6-8.

To quantify the amount of protein inserted into the vesicles, the dialyzed cell-free reactions were subjected to a sucrose floatation assay. The dialyzed reaction is mixed with a dense sucrose solution and loaded at the bottom of a three step sucrose gradient (see FIG. 7). The densities of the layers are chosen such that, after ultracentrifugation (16 hrs, 237000× g), the misfolded protein aggregates (with density p~1.3 g/mL) stay in the bottom layer while the lighter vesicles (p~1.13-1.25 g/mL, depending on how much protein has been inserted) float to the interface above the second layer. FIG. 8 shows the distribution of radiolabeled MtlA after sucrose floatation analysis. 6 M urea has been added throughout the gradients to reduce non-specific association of the synthesized protein with membranes. When vesicles are present in the reaction, we see that 20% of the synthesized MtlA is associated with the vesicles (fraction 2). This association disappears when the vesicles are not added to the protein synthesis reaction, as indicated by the retention of aggregated MtlA in the lower fractions (fractions 6-8). The amount of MtlA shown inserted into vesicles corresponds to an overall yield of 60 μg of inserted MtlA per mL of cell-free reaction, approximately 30 times the typical in vivo yields for MtlA (<2 μg/mL).

Figure 9:
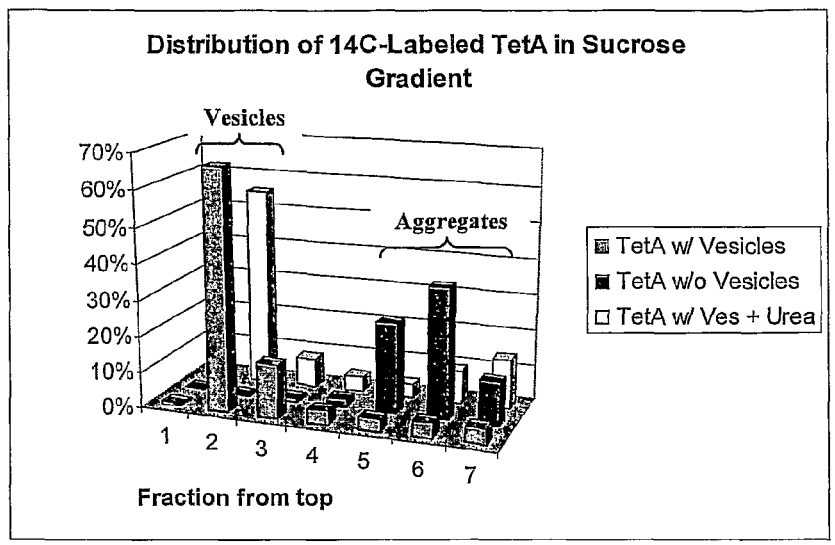
FIG. 9 Distribution of radiolabeled TetA in sucrose flotation assays. Vesicle-associated TetA floats up to fraction 2, while aggregated TetA remains at the bottom of the gradient in fractions 5-7. 6M urea is added to remove TetA that is non-specifically associated with the vesicles.

Even higher yields were obtained for TetA. FIG. 9 shows sucrose floatation profiles for reactions producing TetA. In the presence of vesicles, over 60% of the synthesized TetA is associated with the vesicles (fraction 2). The addition of 6M urea only slightly reduces this value, indicating that the TetA is specifically associated. When the vesicles are not added to the synthesis reaction, the TetA remains aggregated and localizes in fractions 5-7 of the sucrose gradient. The amount of TetA shown inserted into vesicles corresponds to an overall yield of 440 µg of inserted TetA per mL of cell-free reaction, approximately 300 times the typical in vivo yields for TetA (1-1.5 µg/mL).

These data demonstrate that high yields of membrane proteins are synthesized by the methods of the invention, and the synthesized protein is inserted into vesicles and properly folded.

Example 2

TetA Activity Assay

The TetA activity assay is performed similarly to that described in Yamaguchi, et al (1990) J Biol Chem, 265 (9): p. 4809-13. TetA is a proton-antiporter, catalyzing the transport of a metal-tetracycine complex out of the cytoplasm using the cell's natural proton gradient as the driving force.

To assay for TetA activity, a proton gradient is generated across the vesicle membrane by exposing the TetA-containing vesicles to 13.3 mM NADH at 37° C. for a fixed amount of time. The generated pH gradient is quantified using a self-quenching, pH-sensitive fluorescent dye, such as quinacrine (Yamaguchi et al., (1991) FEBS Lett, 282 (2): p. 415-8.) This dye is membrane permeable in its neutral state, but becomes protonated at low pH causing it to be preferentially trapped inside the vesicles after the gradient has been generated. Since the dye is self-quenching, the amount of dye trapped in the vesicles is indicated by a overall drop in fluorescence signal, thereby giving a quantifiable measure of the pH inside the vesicles.

After generation of the pH gradient, 10 µM [$^3$H]-tetracycline and 0.5 mM cobalt chloride is then added, and the reaction is further incubated at 37° C. At specified time intervals, the transported tetracycline is measured by collecting the vesicles and washing using a 30 kD molecular weight centrifugal filter which separates vesicle-associated tetracycline from free tetracycline in solution. The radioactive tetracycline remaining on the filters can then be quantified using a liquid scintillation counter. By combining this data with the measurements of inserted protein from sucrose flotation assays, the rate of tetracycline transport per TetA molecule per unit pH gradient is calculated.

To determine if cell-free produced TetA is fully active, the activity data is compared to vesicles made from *E. coli* strain KC6 expressing TetA in vivo. The activity assay is performed with these vesicles as described above. In order to quantify the number of TetA molecules in the cell-free vesicles, a fifteen amino acid tag is added to the TetA protein which is readily biotinylated by birA ligase (Avidity, LLC). After biotinylation, the vesicles are exposed to radiolabeled streptavidin. By measuring the amount of bound streptavidin, the corresponding amount of TetA contained in the vesicles is calculated.

Example 3

MtlA Activity Assay

Mannitol transport by MtlA is a PEP-driven process involving two other cytoplasmic enzymes, HPr (heat stable, histidyl phosphorylatable protein) and PTS Enzyme I. To assay for MtlA activity, the vesicles are preloaded with mannitol. This can be done either (a) by homogenizing cells in buffer containing mannitol during preparation of the vesicle solution before cell-free synthesis of MtlA or (b) by extruding MtlA-containing vesicles after the cell-free reaction in buffer containing mannitol. After a crude purification by dialysis in a 100 kDa MWCO dialysis bag, any residual HPr (9 kDa) or Enzyme I (63 kDa) carried over from the cell extract is removed.

Known amounts of purified HPr, Enzyme I, and PEP are added to the vesicles to initial transport of MtlA out of the vesicles. After incubation at 37° C. for specified time intervals, the vesicles are collected and washed using a 30 kD molecular weight centrifugal filter which separates vesicle-encapsulated mannitol from free mannitol in solution. The encapsulated mannitol (after release by addition of detergent) or free mannitol is quantified by HPLC. Taking this data with the measurement of inserted protein from sucrose flotation assays, the rate of transport per MtlA molecule is calculated.

To determine if our cell-free produced MtlA is fully active, similar techniques as described above for TetA to produce vesicles containing known amounts of in vivo produced MtlA are used.

Example 4

Expression of Aguaporin

Using the methods described above, the membrane protein, aquaporin Z (AqpZ), is produced in high yields and inserted directly into *E. coli* inner membrane vesicles without the use of detergents or refolding steps.

AqpZ is a 24 kDa with six transmembrane segments that serves as a water-specific channel in the inner membrane of *E. coli* (Ringler, P., et al., Structure of the water channel AqpZ from *Escherichia coli* revealed by electron crystallography. Journal of Molecular Biology, 1999. 291 (5): p. 1181-1190).

Figure 10:
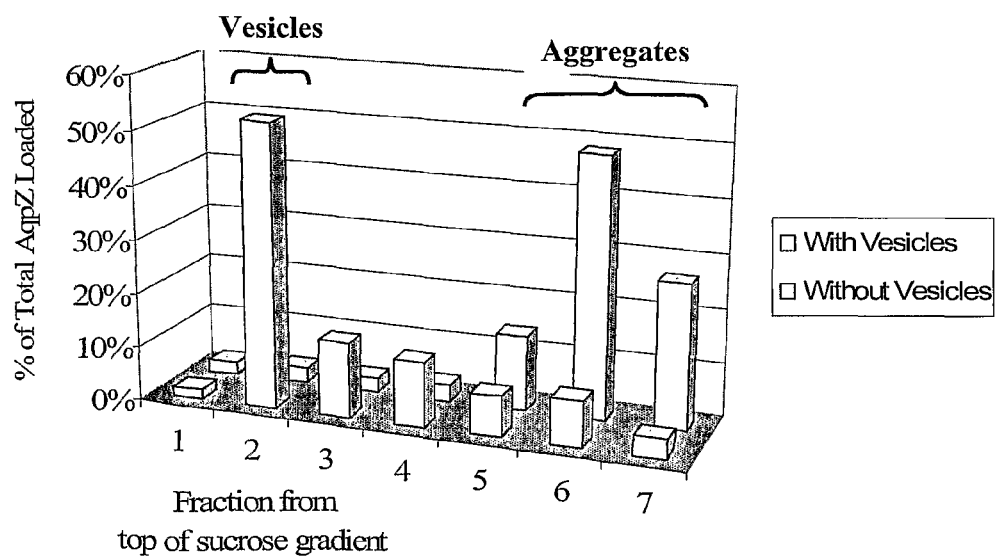
FIG. 10. Distribution of radiolabeled AqpZ in sucrose floatation assays. Vesicle-associated AqpZ floats up to fraction 2, while aggregated AqpZ remains at the bottom of the gradient in fractions 5-7.
Figure 11:
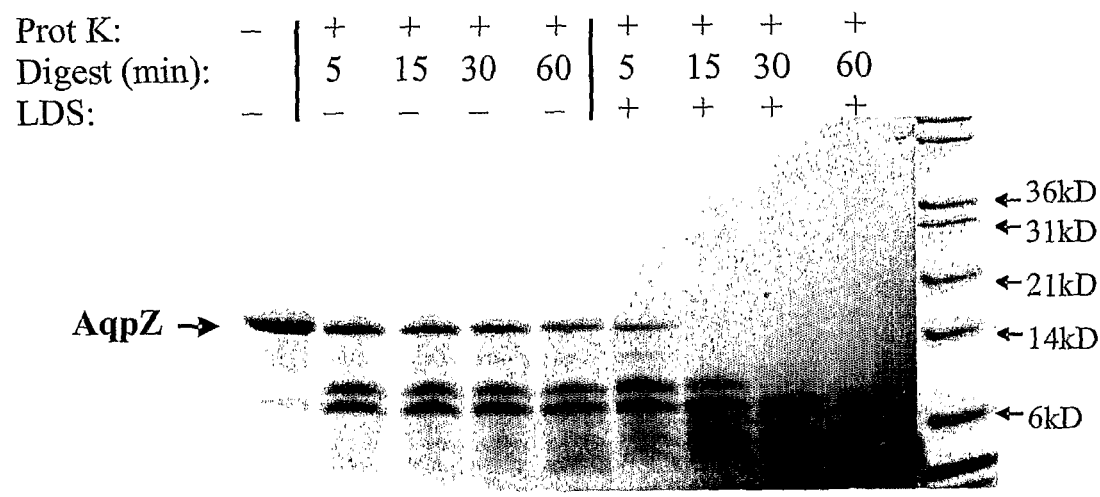
FIG. 11. Autoradiogram of AqpZ samples digested at 37° C. with Proteinase K. Abbreviations: Proteinase K (Prot K), lithium dodecyl sulfate (LDS).

AqpZ was produced in a cytomim-based cell-free reaction, as described above, supplemented with up to 0.6 mg/mL (based on lipid content) of purified inner membrane vesicles. These reactions yielded about 650-800 µg/mL of total AqpZ. To determine how much of this protein is associated with vesicles, we used sucrose floatation to separate the vesicles from any aggregated AqpZ. FIG. 10 shows the distribution of AqpZ in the sucrose gradient. The vesicles, having lower density, float up through the gradient (fraction 2) while the denser aggregates stay at the bottom (fractions 5-7). 6M urea is also present throughout each gradient to minimize nonspecific association of unfolded protein with the vesicles. When vesicles are supplemented in the cell-free reaction, about 50% of the AqpZ is recovered in the vesicle fraction.

In contrast, a reaction in which vesicles are not added shows virtually all of the AqpZ remaining at the bottom of the gradient, presumably in an aggregated form. These results show nearly 400 µg/mL of vesicle-associated AqpZ can be produced in the natural vesicles. This is over 150 times the typical yields obtained when AqpZ is overexpressed in *E. coli* (Borgnia, M. J., et al., Functional reconstitution and characterization of AqpZ, the *E-coli* water channel protein. Journal of Molecular Biology, 1999. 291 (5): p. 1169-1179). The yield of vesicle-associated AqpZ in our cell-free system is similar to that seen with TetA.

Figure 12:
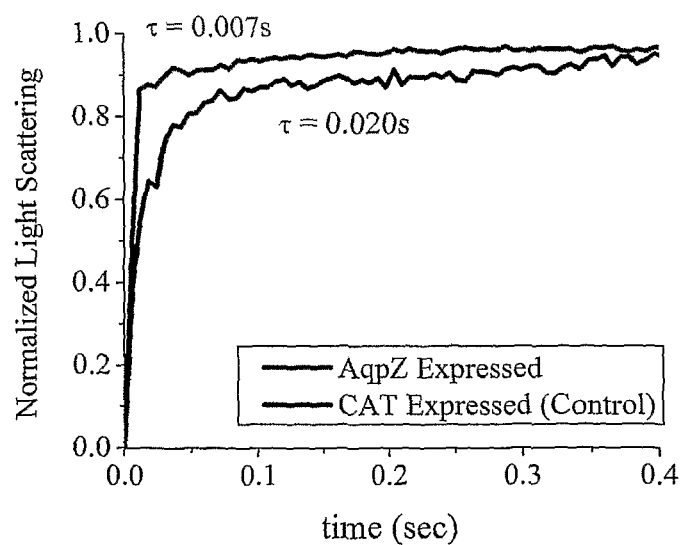
FIG. 12. Rayleigh light scattering measurements monitoring water transport out of vesicles in a hypertonic environement. Vesicles containing synthesized AqpZ show a faster rate of vesicle shrinkage than control vesicles obtained from a control reaction in which an unrelated protein, chloramphenicol acetyl transferase (CAT), was produced.

To determine if the vesicle-associated AqpZ is properly inserted, we subjected the protein to protease digestion. Properly folded AqpZ is known to be resistant to the protease Proteinase K, presumably protected by the surrounding lipid membrane. FIG. 12 shows an autoradiogram in which radiolabeled AqpZ is exposed to the protease for increasing durations. Even after one hour, a significant fraction of the full-length AqpZ remains. In contrast, when the lipid membranes are dissolved using LDS detergent, the AqpZ is no longer protected, showing nearly complete degradation by 15 min. These results suggest that the associated AqpZ is properly inserted into the vesicle membrane.

In addition to protease digestion, we also measured the activity of the produced AqpZ by measuring water transport using stopped-flow static light scattering (Haines, T. H., Water Transport across Biological-Membranes. Febs Letters, 1994. 346 (1): p. 115-122). Vesicles containing the synthesized AqpZ are extruded through a 50 nm membrane. The vesicle solution (0.05 mg/mL lipid basis) is then simultaneously injected into the flow chamber along with a 150 mM sucrose solution. The hypertonic environment causes the vesicles to shrink with time. The shrinkage rate can be monitored by measuring the amount of Rayleigh light scattering that results (FIG. 12). Vesicles containing synthesized AqpZ show much faster shrinkage rates (time constant $\tau$=7 ms) than control vesicles in which an unrelated protein was produced (time constant $\tau$=20 ms). From this data, we calculate a specific activity of $3.7 \times 10^{-14}$ cm$^3$/sec/monomer which matches the specific activities measured for in vivo produced AqpZ ($2\text{-}10 \times 10^{-14}$ cm$^3$/sec/monomer (Pohl, P., et al., Highly selective water channel activity measured by voltage clamp: Analysis of planar lipid bilayers reconstituted with purified AqpZ. Proceedings of the National Academy of Sciences of the United States of America, 2001. 98 (17): p. 9624-9629). Thus, the AqpZ produced in our cell-free system is the same as that produced in vivo.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for synthesis of integral membrane associated polypeptides in a cell-free in vitro reaction, the method comprising:
synthesizing an integral membrane associated polypeptide in a cell-free in vitro translation reaction, where the reaction mixture comprises an extract from bacterial cells; components of polypeptide synthesis machinery; a template for transcription of mRNA and/or translation of said polypeptide; monomers for synthesis of said mRNA and/or polypeptides; and co-factors, enzymes and other reagents necessary for said transcription and/or translation; and vesicles added to a concentration of at least 0.4 mg/ml lipids, wherein the reaction mix produces at least 50 μg/ml of said integral membrane associated polypeptides.

2. The method according to claim 1, wherein said reaction mixture produces at least 100 μg/ml of membrane associated polypeptide.

3. A method for synthesis of integral membrane associated polypeptides in a cell-free in vitro reaction, the method comprising:
synthesizing an integral membrane associated polypeptide in a cell-free in vitro translation reaction, where the reaction mixture comprises an extract from bacterial cells; components of polypeptide synthesis machinery; a template for transcription of mRNA and/or translation of said polypeptide; monomers for synthesis of said mRNA and/or polypeptides; and co-factors, enzymes and other reagents necessary for said transcription and/or translation; and vesicles added to a concentration of at least 0.4 mg/ml lipids, wherein the reaction mix produces at least 50 μg/ml of integral membrane associated polypeptides; and
isolating said integral membrane-associated polypeptide from said reaction mixture under conditions that maintain membrane association of said polypeptide and said vesicles.

4. The method according to claim 1, wherein said reaction mixture comprises signal recognition particles (SRP).

5. The method according to claim 4, wherein said reaction mixture further comprises FtsY protein.

6. The method of claim 1 wherein said synthesis is performed as a batch or fed-batch reaction.

7. The method of claim 1, wherein said synthesis is performed as a continuous reaction.

8. The method of claim 1, wherein said reaction mix comprises an extract from *E. coil* grown in glucose containing medium.

9. The method of claim 8, wherein said *E. coil* are grown in glucose and phosphate containing medium.

10. The method of claim 5, wherein said reaction mix comprises magnesium at a concentration of from about 5 mM to about 20 mM.

11. The method of claim 6, wherein said reaction mix is substantially free of polyethylene glycol.

12. The method according to claim 7, wherein said reaction mix comprises one or more of spermine, spermidine and putrescine.

13. The method of claim 1, wherein the vesicles are purified prior to addition to the reaction mixture.

* * * * *

UNITED STATES PATENT AND TRADEMARK OFFICE
CERTIFICATE OF CORRECTION

PATENT NO. : 8,183,010 B2 Page 1 of 1
APPLICATION NO. : 12/089596
DATED : May 22, 2012
INVENTOR(S) : James Robert Swartz It is certified that error appears in the above-identified patent and that said Letters Patent is hereby corrected as shown below:

In the Claims:

Col. 16, Claim 8 line 44: "*E. Coil*" should read --*E.Coli*--.
Col. 16, Claim 9 line 46: "*E. Coil*" should read --*E.Coli*--.

Signed and Sealed this
Twenty-fifth Day of December, 2012

David J. Kappos
*Director of the United States Patent and Trademark Office*